(12) United States Patent
Tadic et al.

(10) Patent No.: US 8,748,153 B2
(45) Date of Patent: Jun. 10, 2014

(54) BIOSORBENTS FOR THE EXTRACTION OF METALS

(75) Inventors: Davor Cotoras Tadic, Santiago (CL); Pabla Viedma, Santiago (CL); Juan Manuel Gajardo Sandoval, Santiago (CL)

(73) Assignees: Universidad de Chile, Santiago (CL); Biotecnologia del Agua Ltda., Santiago (CL)

( * ) Notice: Subject to any disclaimer, the term of this patent is extended or adjusted under 35 U.S.C. 154(b) by 286 days.

(21) Appl. No.: 13/105,506

(22) Filed: May 11, 2011

(65) Prior Publication Data

US 2012/0024795 A1 Feb. 2, 2012

(30) Foreign Application Priority Data

Jul. 30, 2010 (CL) .................................... 814-2010

(51) Int. Cl.
| | | |
|---|---|---|
| C12N 1/00 | (2006.01) | |
| C12N 11/06 | (2006.01) | |
| C12N 1/20 | (2006.01) | |

(52) U.S. Cl.
CPC .. *C12N 11/06* (2013.01); *C12N 1/20* (2013.01)
USPC ........................ 435/242; 435/252.5

(58) Field of Classification Search
None
See application file for complete search history.

(56) References Cited

U.S. PATENT DOCUMENTS

| | | |
|---|---|---|
| 4,769,223 A | 9/1988 | Volesky et al. |
| 5,296,293 A | 3/1994 | Jobst |
| 5,520,811 A | 5/1996 | Dick et al. |
| 5,789,204 A | 8/1998 | Kogtev et al. |
| 5,824,512 A | 10/1998 | Pazirandeh et al. |
| 6,355,172 B1 | 3/2002 | Diels et al. |
| 6,395,143 B1 | 5/2002 | McHale et al. |
| 7,326,344 B2 | 2/2008 | Cotoras Tadic et al. |
| 2008/0009054 A1 | 1/2008 | Davor et al. |
| 2008/0169238 A1 | 7/2008 | Jesus Simoes Campos Tavares et al. |

OTHER PUBLICATIONS

Brierley et al., "Immobilization of biomass for industrial application of biosorption," Biohydrometallurgical Technologies, Proceedings of the International Biohydrometallurgy Symposium, The Minerals, Metals and Materials Society, Warrendale, PA,1993, 35-44.

Castro et al., "Biomasa de Rhizopus oligosporus como adsorbente de iones metalicos," Microbiologia SEM, 1992, 8:94-105.

Cotoras et al., "Sorption of metal ions by whole cells of Bacillus and Micrococcus," Environmental Technology, 1992, 13:551-559.

Cotoras et al., "Biosorption of metal ions by *Azotobacter vinelandii*," World Journal of Applied Microbiology and Biotechnology, 1992, 8:319-323.

Crini, "Recent developments in polysaccharide-based materials used as adsorbents in wastewater treatment," Prog. Polym. Sci., 200, 30:38-70.

Deng et al., "Removal of trivalent and hexavalent chromium with aminated polyacrylonitrile fibers: performance and mechanisms," Water Research, 2004, 38:2424-2432.

Deng et al., "Characterization of PEI-modified biomass and biosorption of Cu(II), Pb(II) and Ni(II)" Water Res., 2005, 39:2167-2177.

Gadd et al., [1993]. "Microbial Treatment of Metal Pollution—A Working Biotechnology?" Trends Biotechnol., 1993, 11:353-359.

Ghoul et al., "Uptake of heavy metals from synthetic aqueous solutions using modified PEI-silica gels," Water Res, 2003, 37:729-734.

Lu et al., "Biosorption of lead, copper and cadmium by an indigenous isolate Enterobacter sp. J1 possessing high heavy-metal resistance," J Hazard Mater, 2006, 134:80-6.

Nakajima et al., "Copper biosorption by chemically treated *Micrococcus luteus* cells," World J. Microbiol. Biotechnol., 2001, 17:343-7.

Savvaidis et al., "Cooper biosorption byPseudomonas cepacia and other strains," World J Microbiol and BioTechnol., 2003, 19:117-21.

Tunali et al., "Removal of lead and copper ions from aqueous solutions by bacterial strain isolated from soil," Chem Eng J, 2006, 115:203-11.

Vijayaraghavan et al., "Bacterial Biosorbents and Biosorption," Biotechnology Advances, 2008, 26:266-291.

*Primary Examiner* — Allison Ford
*Assistant Examiner* — Michelle F Paguio Frising
(74) *Attorney, Agent, or Firm* — Fish & Richardson P.C.

(57) ABSTRACT

A biosorbent for removing cationic and/or anionic metals from aqueous solutions, and a process for the production of the biosorbent. The biosorbent includes bacterial aggregates of *Bacillus* sp. VCHB-10, deposited as NRRL-B-30881, and treated with polyethyleneimine and glutaraldehyde. Among the metals in their cationic form, the following are considered: cations of Ag, Al, Au, Co, Cd, Cu, Cr, Fe, Hg, Mn, Ni, Pb, Pd, Pt, U, Th and Zn. Among the metals in their anionic form, the following are considered: anions of As, Cr and Mo. Removal or recovery of metals from wastewater using the biosorbent is also described.

19 Claims, 9 Drawing Sheets

BIOSORBENTS FOR THE EXTRACTION OF METALS

CROSS-REFERENCE TO RELATED APPLICATION

This application claims priority to Chilean Patent Application No. 814-2010, filed Jul. 30, 2010, which is incorporated herein by reference.

TECHNICAL FIELD

This invention refers to a biosorbent, and a process for the production thereof, for the removal of cationic or anionic metals from aqueous solutions.

BACKGROUND

Biosorption is the uptake of heavy metals by the biomass (living or dead) by distinctly physical-chemical mechanisms. In general, the biosorption process has been described as a non selective mechanism that permits the removal of the following metals, among others: Ag, Al, Au, Co, Cd, Cu, Cr, Fe, Hg, Mn, Ni, Pb, Pd, Pt, U, Th and Zn (Gadd and White (1993), Microbial Treatment of Metal Pollution—A Working Biotechnology? Trends Biotechnol., 11, 353-359).

At present there is abundant scientific literature in the international sphere on the capacity of some microorganisms to concentrate metal ions by biosorption from diluted solutions, including Castro et al (1992), Biomasa de *Rhizopus oligosporus* como adsorbente de iones metálicos. Microbiologia SEM 8, 94-105, Cotoras et al. (1992), Biosorption of metal ions by *Azotobacter vinelandii*. World Journal of Applied Microbiology and Biotechnology 8, 319-323, Cotoras et al. (1992) Sorption of metal ions by whole cells of *Bacillus* and *Micrococcus* Environmental Technology 13, 551-559. Research has covered different groups of organisms, including bacteria (for example, *E. coli, Zoogloea ramigera, Bacillus subtilis, Azotobacter vinelandii*, etc.), fungii (Example, *Rhizopus arrhizus, Aspergillus niger*) and algae (for example, *Chlorella vulgaris, Sargassum* sp.). From all these works, microorganisms appear to be capable of concentrating appreciable amounts of metal ions.

Bacteria of the *Bacillus* genus, among others, have been used as biosorbents of copper, Tunali S, Ç abuk A, Akar T. Removal of lead and copper ions from aqueous solutions by bacterial strain isolated from soil. Chem Eng J 2006; 115: 203-11; Nakajima A, Yasuda M, Yokoyama H, Ohya-Nishiguchi H, Kamada H. Copper biosorption by chemically treated *Micrococcus luteus* cells. World J. Microbiol. Biotechnol. 2001; 17:343-7; Cotoras D., Viedma P., Cifuentes L. and Mestre A. Sorption of metal ions by whole cells of *Bacillus* and *Micrococcus* Environmental Technology 13, 551-559 (1992); U.S. Pat. No. 7,326,344; U.S. Patent Application Publication No. 2008/0009054; Enterobacter, Lu W-B, Shi J-J, Wang C-H, Chang J-S. Biosorption of lead, copper and cadmium by an indigenous isolate *Enterobacter* sp. J1 possessing high heavy-metal resistance. J Hazard Mater 2006; 134:80-6 o *Pseudomonas*, Savvaidis I, Hughes M N, Poole R K. Copper biosorption by *Pseudomonas cepacia* and other strains. World J. Microbiol. Biotechnol. 2003; 19:117-21.

Recent efforts have centered on the chemical modification of the biomass by means of the insertion of functional groups such as amine, carboxyl and hydroxyl to achieve considerable increases in the biosorbent capacity and at the same time obtain the stabilization of the biomass used maintaining the biosorption efficiency after repeated cycles of adsorption/regeneration of the biomass, Vijayaraghavan K., Yun Y S. Bacterial Biosorbents and Biosorption. Biotechnology Advances 26 (2008) 266-291; Diaz de Apodaca E, Villarán M C, Rio F, Ramirez C A, Ibarreña L. Utilization of adsorbents based on chitosan and sodium alginate for the elimination of metal ions: $Cu^{2+}$, $Pb^{2+}$, $Cr^{3+}$ y $Co^{2+}$. Revista Iberoamericana de Polimeros Volumen 8(1), 2007; Ghoul M, Bacquet M., Morcellet M., Uptake of heavy metals from synthetic aqueous solutions using modified polyethyleneimine-silica gels, Water Res 37 (2003), pp. 729-734; Deng S, and Ting Y. P. Characterization of polyethyleneimine-modified biomass and biosorption of Cu(II), Pb(II) and Ni(II) Water Res. 39 (2005), pp. 2167-2177; Deng S, Bai R. Removal of trivalent and hexavalent chromium with aminated polyacrylonitrile fibers: performance and mechanisms. Water Research 38 (2004) 2424-2432; Crini G. Recent developments in polysaccharide-based materials used as adsorbents in wastewater treatment. Prog. Polym. Sci. 30 (2005) 38-70.

Commercial-type biosorbents have been developed, but due to the complexity of their production procedures they become transformed into technologies that are expensive and not very environment-friendly, Brierley C. L. and J. A. Brierley, Immobilization of biomass for industrial application of biosorption. In: A. E. Torma, M. L. Apel and C. L. Brierley, Editors, Biohydrometallurgical Technologies, Proceedings of the International Biohydrometallurgy Symposium, The Minerals, Metals and Materials Society, Warrendale, Pa. (1993), pp. 35-44; U.S. Pat. Nos. 6,395,143; 5,824,512; 5,789,204; 5,520,811; 4,769,223; 5,296,293; and 6,355,172; and U.S. Patent Application Publication No. 2008/0169238.

SUMMARY

In one aspect, a process for the production of biosorbents for removing cationic or anionic metals from aqueous solutions includes:
  a) growing the bacterial strain *Bacillus* sp. VCHB-10, deposited as NRRL-B-30881, and forming spontaneous aggregates of bacterial cells;
  b) allowing the aggregates of bacterial cells to sediment in order to concentrate the aggregates, removing the culture medium and washing with water;
  c) contacting the aggregates of concentrated bacterial cells with a solution of polyethyleneimine in methanol and allowing to react;
  d) contacting the aggregates of concentrated bacterial cells treated with polyethyleneimine with a solution of glutaraldehyde; and
  e) allowing to sediment and washing with water to obtain the biosorbent.

In an embodiment, the solution of polyethyleneimine has a concentration in the reaction mixture between 0.5% and 10% w/v.

In another embodiment, the solution of polyethyleneimine has a concentration in the reaction mixture between 2% and 8% w/v.

In another preferred embodiment, the solution of polyethyleneimine has a concentration in the reaction mixture between 1% and 4% w/v.

In an embodiment, the solution of glutaraldehyde has a concentration between 0.1% and 2% v/v.

In another embodiment, the solution of glutaraldehyde has a concentration between 0.15% and 1.5% v/v.

In another preferred embodiment, the solution of glutaraldehyde has a concentration between 0.2% and 0.5% v/v.

In another preferred embodiment, the process also includes a step of washing the biomass stabilized with acid, followed by neutralization with base.

In another preferred embodiment, the acid is selected from the group that includes sulfuric acid, hydrochloric acid or phosphoric acid and the base is selected from the group that includes sodium hydroxide or potassium hydroxide.

In another aspect, a biosorbent for removing metals from aqueous solutions includes bacterial aggregates of *Bacillus* sp. VCHB-10, deposited as NRRL-B-30881, treated with polyethyleneimine and crosslinked with glutaraldehyde.

In another aspect, a biosorbent is capable of removing metals in their cationic and anionic forms.

Among the metals in their cationic form, the following are considered: Ag, Al, Au, Co, Cd, Cu, Cr, Fe, Hg, Mn, Ni, Pb, Pd, Pt, U, Th and Zn.

Among the metals in their anionic form, the following are considered: As, Cr and Mo.

In another aspect, a process for the removal or recovery of metals from wastewaters using the biosorbent includes:
  a) contacting water that contains metal ions with the biosorbent to remove the metal ions by biosorption, allowing the biosorbent to sediment, removing the treated water, contacting the water that contains metal ions with the biosorbent as often as necessary until its biosorption capacity starts to diminish due to the saturation;
  b) allowing the biosorbent to sediment and removing the remaining water;
  c) adding an inorganic acid to elute the metal ions captured by the bacterial cell aggregates; and
  d) repeating the process starting from step a.

The following examples illustrate some specific applications, but do not limit the framework or the scope of this disclosure.

DETAILED DESCRIPTION

A process for the production of biosorbents for removing cationic or anionic metals from aqueous solutions is described herein. Also described is a biosorbent for the removal of metals from aqueous solutions that includes bacterial aggregates of *Bacillus* sp. VCHB-10, treated with polyethyleneimine and crosslinked with glutaraldehyde. This strain has been deposited on 28 Oct. 2005 in the international collection Agricultural Research Service Culture Collection NRRL, with the access number NRRL-B-30881.

Use of the biosorbent for removing metals in their cationic and anionic forms is also described. Among the metals in their cationic form, the following are considered, including cations of Ag, Al, Au, Co, Cd, Cu, Cr, Fe, Hg, Mn, Ni, Pb, Pd, Pt, U, Th or Zn. Among the metals in their anionic form, the following are considered, including anions of As, Cr or Mo. A process is also disclosed for the removal or recovery of metals from wastewater using the biosorbent.

A solution having bacterial aggregates can be formed spontaneously by the bacteria *Bacillus* sp. (VCHB-10). These bacterial aggregates sediment readily due, for example, to the size of the aggregates. This sedimentation facilitates biomass recovery in the cultivation stage and in the biosorption/regeneration cycles. Chemical modification stages also include separating the treated biomass by sedimentation. In a similar manner, separation of the biomass can be achieved during the repeated cycles of biosorption and desorption. The resulting biosorbent can include one or more of the following benefits relative to the same biomass that is chemically untreated (unmodified):
  Increase from 2 to 3 times in the biosorption capacity.
  Biosorption capacity that is maintained after repeated cycles of adsorption/desorption of the metal.
  Better and quicker sedimentation by the formation of larger size bacterial aggregates.
  Less loss of biomass between adsorption/desorption cycles of the metal.

- Diminution of important cell remnants loaded with metals in the solution treated.
- Uptake capacity at low concentrations of metal ensuring the compliance with the discharge standards of metals in industrial liquid waste.
- Stabilized product capable of being reused without the need for expensive centrifugation processes.
- Greater resistance to aggressive mechanical forces such as agitation.

EXAMPLES

Example 1

The bacterial strain of *Bacillus* sp. VCHB-10 (NRRL-B-30881) was cultivated executing a transfer from a stock culture to one in TSA agar under a laminar flow hood and incubated for 24 hours at 28° C. A 250 mL flask with 100 mL of sterile culture medium was inoculated with an agar slant culture of the strain recently activated under a laminar flow hood and incubated in an orbital shaker for 24 hours at 150 rpm and 28° C. The composition of the liquid culture medium for the cultures of the strain of *Bacillus* sp. VCHB-10, NRRL-B-30881 is shown in the following Table 1.

TABLE 1

Composition of culture medium for the strain of *Bacillus* sp. VCHB-10, NRRL-B-30881.

| Component | Concentration |
|---|---|
| $Na_2HPO_4 \cdot 2H_2O$ | 1.254 g/L |
| $KH_2PO_4$ | 0.3 g/L |
| $K_2SO_4$ | 0.1 g/L |
| NaCl | 0.1 g/L |
| $MgSO_4 \cdot 7H_2O$ | 0.02 g/L |
| $CaCl_2 \cdot 2H_2O$ | 0.01325 g/L |
| $FeSO_4 \cdot 7H_2O$ | 0.00183 g/L |
| Yeast extract | 1.0 g/L |
| Tryptone | 1.0 g/L |
| Glucose | 10.0 g/L |

The glucose was prepared separately. Both solutions were autoclaved at 121° C. for 15 minutes.

The bacterial aggregates of *Bacillus* sp. VCHB-10 formed in 100 mL of a culture of 24 hours were decanted for 30 minutes in a separating funnel, were recovered in a 250 mL flask and were stored at 3° C. The biomass present was measured using the dry weight method.

Subsequently, these bacterial aggregates of *Bacillus* sp. VCHB-10 were stabilized with polyethyleneimine and glutaraldehyde as is explained below.

A polyethyleneimine solution at 10% w/v was prepared by mixing 10 mL of the flocculated biomass, 30 mL of pure methanol (Merck) and 10 mL of the polyethyleneimine solution at 50% w/v (Sigma), which was gently agitated for 24 hours at room temperature and later combined with a solution containing 2.5 mL of glutaraldehyde at 25% (Merck) dissolved beforehand in 197.5 mL of distilled water, thus obtaining a final concentration of 1% v/v of glutaraldehyde. It was agitated gently and allowed to react for 20 minutes. The resulting modified biomass was washed with distilled water and was recovered in all the stages in accordance with the sedimentation protocol described above.

The stabilized aggregates of *Bacillus* sp. VCHB-10 were used to remove copper from a solution. To do this, the stabilized biomass was suspended in 120 mL of a solution of 20 mg/L of copper in the form of a pentahydrated sulfate and was shaken for 30 minutes at 150 rpm and 28° C. The biosorbent was decanted for 30 minutes in a separating funnel. The supernatant was separated and stored for its later analysis. The copper adsorbed by the biosorbent was recovered by adding 60 mL of a solution of sulfuric acid (pH 1.0) and incubating for 30 minutes at 150 rpm and 28° C. Subsequently the biosorbent was decanted for 30 minutes in a separating funnel. The acid eluate containing the copper was separated and stored for its later analysis. Finally, the biomass was washed with a solution of NaOH (pH 11) and the biosorbent was decanted for 30 minutes in a separating funnel.

Figure 1:
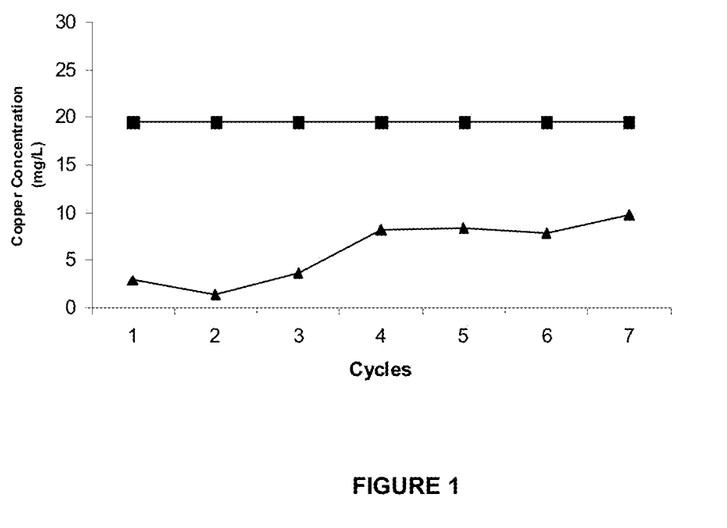
FIG. 1 shows the concentration of copper in the supernatant of the residual solution after contacting, in seven consecutive cycles of biosorption/regeneration, the added bacteria of *Bacillus* sp. (VCHB-10) treated with polyethyleneimine and glutaraldehyde with 120 mL of a copper solution of 20 mg/L during 30 minutes, at 150 rpm and 28° C.

FIG. 1 shows the concentration of copper in the supernatant of the residual solution after contacting, in seven consecutive cycles of biosorption/regeneration, the added bacteria of *Bacillus* sp. (VCHB-10) treated with polyethyleneimine and glutaraldehyde with 120 mL of a copper solution of 20 mg/L during 30 minutes, at 150 rpm and 28° C. The squares represent the concentration value of the initial sample of copper added to the biosorbent without treatment and the triangles represent the concentration of the solution of the supernatant after each stage of copper biosorption. It is evident during cycles 1, 2 and 3 that the concentration of the copper dropped from 20 mg/L to values below 4 mg/L, and reached a minimum of 1.40 mg/L in cycle 2. Subsequently, from cycles 4 to 7, the concentration in the remaining solution increased and was maintained between 8-9 mg/L.

Figure 2:
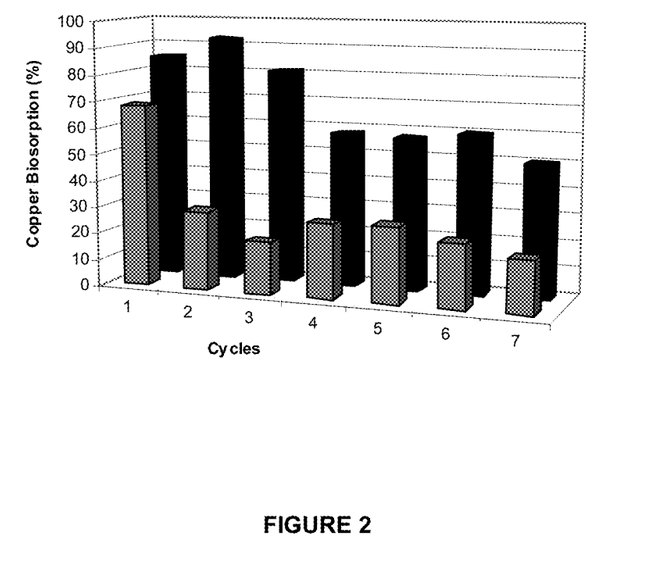
FIG. 2 shows the percentage of copper adsorbed by added bacteria of *Bacillus* sp. (VCHB-10) treated and not treated with polyethyleneimine and glutaraldehyde after each biosorption.

FIG. 2 shows the percentage of copper adsorbed by added bacteria of *Bacillus* sp. (VCHB-10), treated and not treated with polyethyleneimine and glutaraldehyde, after each biosorption. The bars in black correspond to the percentage of copper captured by added bacteria of *Bacillus* sp. (VCHB-10) treated with polyethyleneimine and glutaraldehyde (the modified biosorbent), and the bars in grey correspond to the percentage of copper captured by added bacteria of *Bacillus* sp. (VCHB-10) without treatment (the unmodified biosorbent). A high capacity of biosorption and stability of the modified biosorbent was observed: the modified biosorbent was still able to remove 50% of the copper after 7 cycles of biosorption/desorption. In contrast, decreased biosorption capacity was observed for the non-modified biosorbent, with the second and subsequent cycles of biosorption/desorption showing 20%-30% adsorption of copper present in the initial solution.

Figure 3:
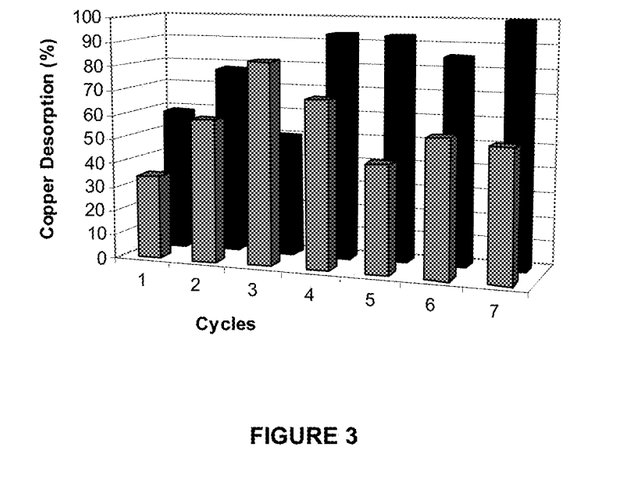
FIG. 3 shows the percentage of copper desorbed from added bacteria of *Bacillus* sp. (VCHB-10) treated and not treated with polyethyleneimine and glutaraldehyde after each biosorption.

FIG. 3 shows the percentage of copper desorbed via acid desorption from added bacteria of *Bacillus* sp. (VCHB-10), treated and not treated with polyethyleneimine and glutaraldehyde, after each biosorption. The bars in black correspond to the percentage of copper extracted from added bacteria of *Bacillus* sp. (VCHB-10) treated with polyethyleneimine and glutaraldehyde (the modified biosorbent), and the bars in grey correspond to the percentage of copper extracted from added bacteria of *Bacillus* sp. (VCHB-10) without treatment (the unmodified biosorbent). A high capacity of desorption of the modified biosorbent was observed, and was maintained until the 7th cycle of biosorption/desorption. The unmodified biosorbent shows copper recovery values between 34% and 83% during the 7 cycles of treatment.

Example 2

The cultivation of the strain *Bacillus* sp. VCHB-10 and the recovery of bacterial aggregates formed were carried out in the same manner as in Example 1.

The non-stabilized (unmodified) bacterial aggregates were used to execute a metal biosorption process. To do this, 10 mL of the non-stabilized flocculated biomass of *Bacillus* sp. VCHB-10 was suspended in 120 mL of a solution of 26 mg/L of copper in the form of pentahydrated sulfate and was shaken for 30 minutes at 150 rpm and 28° C. The biosorbent was decanted for 30 minutes in a separating funnel. The supernatant was separated and stored for subsequent analysis. The copper adsorbed by the biosorbent was recovered by adding 60 mL of a solution of sulfuric acid (pH 2.2) and incubating for 30 minutes at 150 rpm and 28° C. Subsequently, the biosorbent was decanted for 30 minutes in a separating funnel. The acid eluate that contains copper was separated and stored for its subsequent analysis. Finally, the biomass was washed with a solution of NaOH (pH 11) and the biosorbent was decanted for 30 minutes in a separating funnel.

The total concentration of copper in the supernatants in the stages of biosorption and desorption was measured in a Hanna Instruments photometer Series C99&C200.

Figure 4:
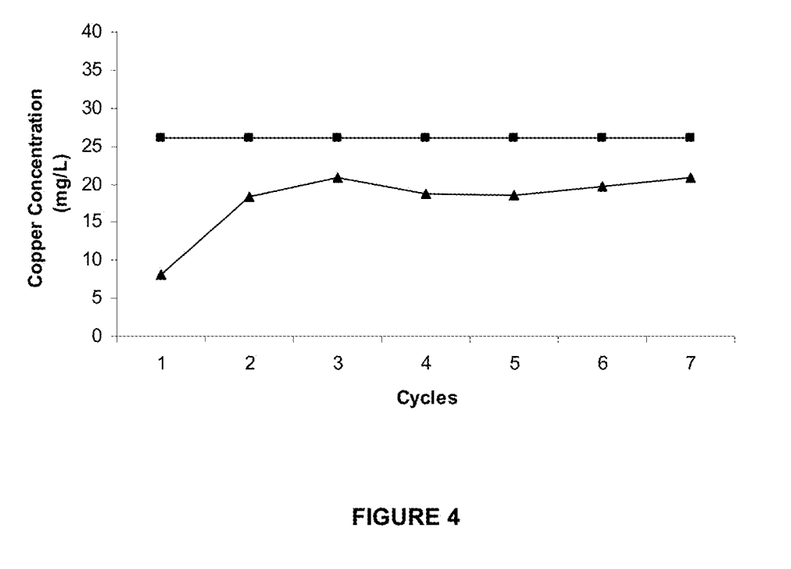
FIG. 4 shows the concentration of copper in the supernatant of the residual solution after contacting, in seven consecutive cycles of biosorption/regeneration, the added bacteria of *Bacillus* sp. (VCHB-10) without stabilization treatment with 120 mL of a copper solution of 26 mg/L during 30 minutes, at 150 rpm and 28° C.

FIG. 4 shows the concentration of copper in the supernatant of the residual solution after contacting, in seven consecutive cycles of biosorption/regeneration, the added bacteria of *Bacillus* sp. (VCHB-10) without stabilization treatment with 120 mL of a copper solution of 26 mg/L during 30 minutes, at 150 rpm and 28° C. The squares represent the concentration value of the initial sample of copper added to the untreated biosorbent and the triangles represent the concentration of the solution of supernatant after each stage of biosorption of the copper. In the first cycle of biosorption the concentration of copper of the initial solution or standard dropped from 26 mg/L to 8.2 mg/L equivalent for a 69% copper uptake. Nevertheless, as of the 2nd cycle, the concentration of the remaining solution increased and started to come closer to the value of the initial solution to then remain firm between 18 mg/L and 21 mg/L.

FIG. 2 permits a comparison between Examples 1 and 2. The greater stability and efficiency in copper removal of the modified biosorbent solution with regard to the unmodified biosorbent can be seen very clearly. In the first cycle, the difference between both is 16.6%. Nevertheless, this difference is accentuated in the second and seventh cycles. Moreover, FIG. 3 generally shows a greater recovery of the copper from the modified biosorbent than the unmodified biosorbent.

According to the results obtained, one may be able to conclude that the modification of the biosorbent using polyethyleneimine and glutaraldehyde increases the stability of the bacterial aggregates of *Bacillus* sp. (VCHB-10), making it possible to maintain and improve the copper adsorption capacity even after 7 cycles of biosorption/regeneration in comparison with the unmodified or untreated bacterial aggregates of *Bacillus* sp. (VCHB-10).

Example 3

The cultivation of the *Bacillus* sp. VCHB-10 strain and the recovery of the bacterial aggregates formed were carried out in the same way as in Example 1. Subsequently, these bacterial aggregates were treated with different concentrations of polyethyleneimine and glutaraldehyde at 1% of the strain of *Bacillus* sp. VCHB-10, as explained below.

The solution of polyethyleneimine at 1% w/v was prepared by mixing 10 mL of the flocculated biomass, 39 mL of pure methanol (Merck) and 1 mL of a solution of polyethyleneimine at 50% w/v (Sigma), which was shaken gently for 24 hours at room temperature and later combined with a solution containing 2.5 mL of glutaraldehyde at 25% (Merck) dissolved beforehand in 197.5 mL of distilled water, thus obtaining a final concentration of 1% v/v of glutaraldehyde. It was shaken gently and left to react for 20 minutes. The resulting modified biomass was washed with distilled water and was recovered in all the stages according to the sedimentation protocol described previously.

The solution of polyethyleneimine at 2% w/v was prepared by mixing 10 mL of the flocculated biomass, 38 mL of pure methanol (Merck) and 2 mL of a solution of polyethyleneimine at 50% w/v (Sigma), which was gently agitated for 24 hours at room temperature and later combined with a solution containing 2.5 mL of glutaraldehyde at 25% (Merck) dissolved previously in 197.5 mL of distilled water, thus obtaining a final concentration of 1% v/v of glutaraldehyde. It was agitated gently and left to react for 20 minutes. The resulting modified biomass was washed with distilled water and was recovered in all the stages according to the sedimentation protocol described previously.

The solution of polyethyleneimine at 4% w/v was prepared by mixing 10 mL of the flocculated biomass, 36 mL of pure methanol (Merck) and 4 mL of a solution of polyethyleneimine at 50% w/v (Sigma), which was gently agitated for 24 hours at room temperature and later combined with a solution containing 2.5 mL of glutaraldehyde at 25% (Merck) dissolved previously in 197.5 mL of distilled water, thus obtaining a final concentration of 1% v/v of glutaraldehyde. It was agitated gently and left to react for 20 minutes. The resulting modified biomass was washed with distilled water and was recovered in all the stages according to the sedimentation protocol described previously.

The solution of polyethyleneimine at 6% w/v was prepared by mixing 10 mL of the flocculated biomass, 34 mL of pure methanol (Merck) and 6 mL of a solution of polyethyleneimine at 50% w/v (Sigma), which was maintained gently agitated for 24 hours at room temperature and later combined with a solution containing 2.5 mL of glutaraldehyde at 25% (Merck) dissolved previously in 197.5 mL of distilled water, thus obtaining a final concentration of 1% v/v of glutaraldehyde. It was agitated gently and left to react for 20 minutes. The resulting modified biomass was washed with distilled water and was recovered in all the stages according to the sedimentation protocol described previously.

The solution of polyethyleneimine at 8% w/v was prepared by mixing 10 mL of the flocculated biomass, 32 mL of pure methanol (Merck) and 8 mL of a solution of polyethyleneimine at 50% w/v (Sigma), which was gently agitated for 24 hours at room temperature and later combined with a solution containing 2.5 mL of glutaraldehyde at 25% (Merck) dissolved previously in 197.5 mL of distilled water, thus obtaining a final concentration of 1% v/v of glutaraldehyde. It was agitated gently and left to react for 20 minutes. The resulting modified biomass was washed with distilled water and was recovered in all the stages according to the sedimentation protocol described previously.

The solution of polyethyleneimine at 10% w/v was prepared by mixing 10 mL of the flocculated biomass, 30 mL of pure methanol (Merck) and 10 mL of a solution of polyethyleneimine at 50% w/v (Sigma), which was gently agitated for 24 hours at room temperature and later combined with a solution containing 2.5 mL of glutaraldehyde at 25% (Merck) dissolved previously in 197.5 mL of distilled water, thus obtaining a final concentration of 1% v/v of glutaraldehyde. It was agitated gently and left to react for 20 minutes. The resulting modified biomass was washed with distilled water and was recovered in all the stages according to the sedimentation protocol described previously.

The stabilized aggregates of *Bacillus* sp. VCHB-10 were employed for the removal of copper from a solution. To do this, each preparation of stabilized biomass of *Bacillus* sp. or biosorbent was suspended in 120 mL of a solution of 20 mg/L of copper in the form of pentahydrated sulfate and was agitated during 30 minutes at 150 rpm and 28° C. The biosorbent was decanted for 30 minutes in a separating funnel. The supernatant was separated and stored for its subsequent analysis. The copper adsorbed by the biosorbent was recovered by adding 20 mL of a solution of sulfuric acid (pH 1.0) and incubating for 30 minutes at 150 rpm and 28° C. Subsequently, the biosorbent was decanted for 30 minutes in a separating funnel. The acid eluate that contained copper was separated and stored for its subsequent analysis. Finally, the biosorbent was washed with a solution of NaOH (pH 11) and the biosorbent was decanted for 30 minutes in a separating funnel.

Figure 5:
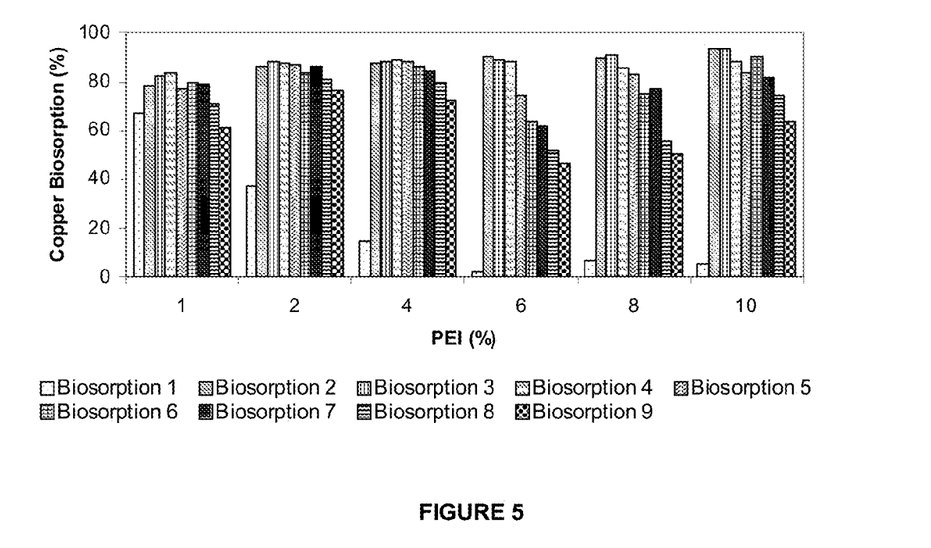
FIG. 5 shows the copper uptake percentage with the biomass of *Bacillus* sp. modified with different percentages of polyethyleneimine and 1% of glutaraldehyde.

FIG. 5 suggests that the biomass treated with the different concentrations of polyethyleneimine permits the execution of numerous cycles of biosorption/desorption. According to FIG. 5, during the first cycle of biosorption (biosorption 1), one can see a high percentage of biosorption when 1% of polyethyleneimine is used. On the other hand, this percentage drops when 2%, 4%, 6%, 8% and 10% of polyethyleneimine is used; this drop may be attributed to the more intense requirements of biosorbent washing after its preparation with these concentrations of polyethyleneimine.

As of the second cycle (biosorption 2), the biosorbent recovers its adsorption capacity in all the percentages of polyethyleneimine studied, reaching values close to 80% for 1% of polyethyleneimine and above 80% for 2%, 4%, 6%, 8% and 10% of polyethyleneimine. This biosorbent capacity is maintained between 60% and 80% during the 7 subsequent cycles carried out (biosorptions 3-9), for the modifications with 1%, 2%, 4% and 10% of polyethyleneimine. Thus, good biosorption results of biosorption can be obtained using polyethyleneimine at least in range between 1% and 4%.

Figure 6:
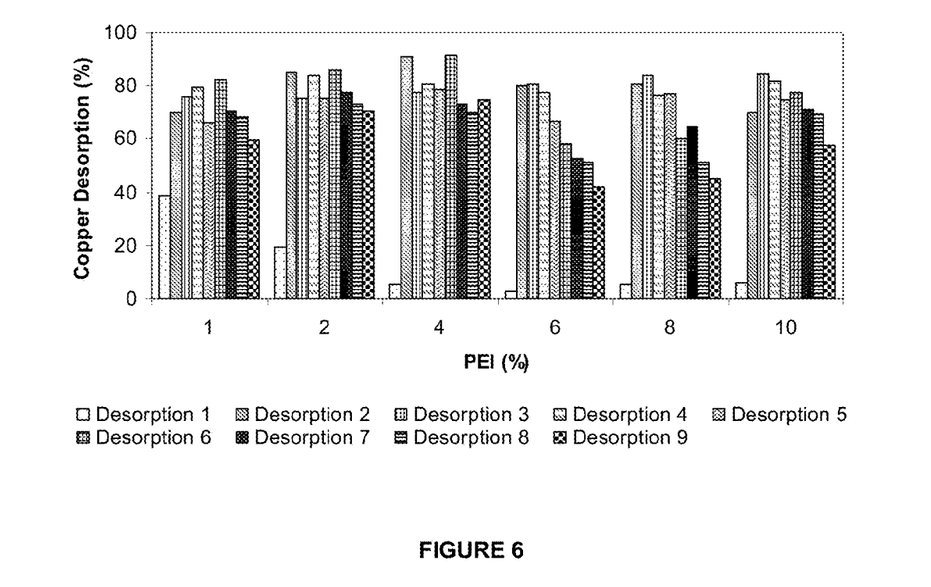
FIG. 6 shows the percentage of desorption of copper with biomass of *Bacillus* sp. modified with different percentages of polyethyleneimine and 1% of glutaraldehyde.

The percentages of desorption of the copper captured by the biosorbents treated with different concentrations of polyethyleneimine are shown in FIG. 6. A high level of copper desorption is observed in the different treatment cycles. The amount of released copper follows the same trend of the previous stage of biosorption (FIG. 5).

Example 4

The preculture of the strain Bacillus sp. VCHB-10 was inoculated from a TSA agar slant culture, in the same manner as described in Example 1. After 24 hours of incubation, 1.5 mL of the preculture was taken to inoculate the fermenter (New Brunswick Scientific Multigen F-1000®) with 1.5 L of sterile medium of the same composition, which was incubated for 16 hours at 28° C., 200 rpm, and 0.75 vvm of aeration. Once the culture was finished, the obtained bacterial aggregates were recovered by sedimentation with a separating funnel in the same manner as described previously.

The process of immobilization of the bacterial aggregates of Bacillus sp. VCHB-10 was carried out with a solution at 1% w/v of polyethyleneimine, employing different concentrations of glutaraldehyde (0.2%, 0.5%, 1.0% and 1.5%). To do this, 10 mL of flocculated biomass, 39 mL of methanol p.a. (Merck®) and 1 mL of a solution of polyethyleneimine 50% w/v (Sigma®) in duplicate were mixed in 500 mL Erlenmeyer flasks. The mixture was shaken smoothly at room temperature for 24 hours and later transferred to each solution of glutaraldehyde as explained below:

The solution of glutaraldehyde at 0.2% v/v was prepared adding the biomass treated with polyethyleneimine 1% to a solution that contained 0.5 mL of glutaraldehyde at 25% w/v and 199.5 mL of distilled water, thus obtaining a final solution of 0.2% v/v. The same procedure was carried out to prepare the other solutions: The solution at 0.5% v/v was prepared adding the biomass to a solution that contained 1.25 mL of glutaraldehyde 25% w/v and 198.75 mL of distilled water; the solution at 1% w/v adding the biomass to a solution that contained 2.5 ml of glutaraldehyde 25% w/v and 197.5 mL of distilled water; and finally, the solution at 1.5% v/v was prepared adding the biomass to a solution that contained 3 mL of glutaraldehyde 25% w/v and 197 mL of distilled water. Each resulting solution was incubated for 20 minutes at room temperature to finally recover the bacterial aggregates in a separating funnel in the same manner described previously.

The stabilized bacterial aggregates were used to execute a process of biosorption of metals. To do this, each fraction of stabilized biomass was submitted to the biosorption process according to the process described in Example 1. Subsequently, the total concentration of copper present in the aliquots of biosorption and desorption was measured in a Hanna Instruments® photometer Series C99&C200.

Figure 7:
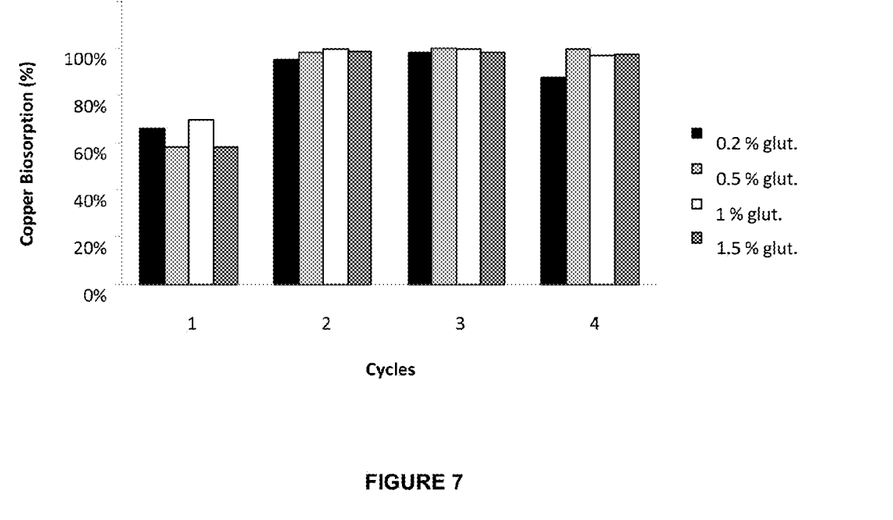
FIG. 7 shows the percentage of copper captured by the biomass stabilized with 0.2; 0.5; 1 and 1.5% v/v of glutaraldehyde.

FIG. 7 shows that the biomass stabilized with 0.2% v/v of glutaraldehyde recovered 66.1% of the copper in the initial solution, and the biomass stabilized with 0.5%, 1% and 1.5% of glutaraldehyde recovered 58.4%, 69.5% and 58.4% of the copper in the initial solution, respectively. In the second cycle, the biosorption increased in all the cases, rising to over 95%. This trend was maintained in the third and fourth cycles.

Figure 8:
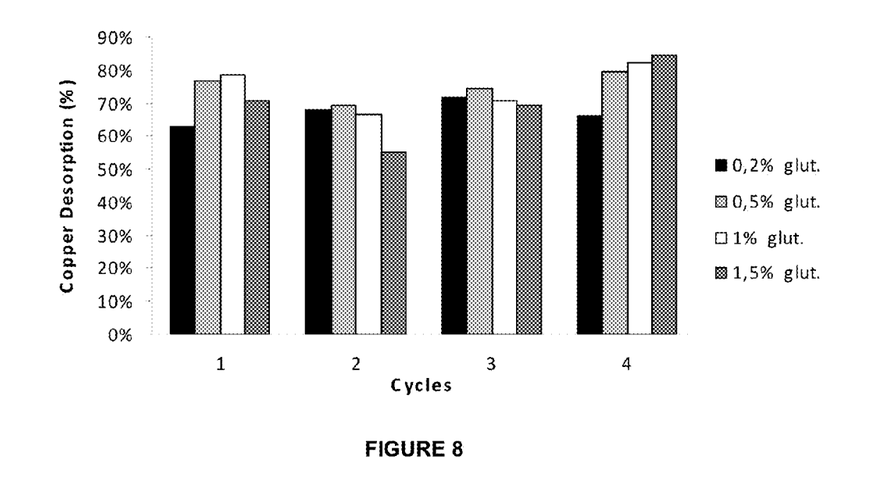
FIG. 8 shows the percentage of copper desorbed by the biomass stabilized with 0.2; 0.5; 1 and 1.5% v/v of glutaraldehyde.

With regard to the desorption (FIG. 8), the biomass treated with 1% of glutaraldehyde recovered between 60% and 80% of the total copper in the standard solution in the fourth cycle, unlike the biomass treated with another percentage of glutaraldehyde.

According to the results obtained in this experiment, the biomass treated with 0.2-1.5% v/v of glutaraldehyde presented a high capacity of biosorption and desorption.

Example 5

The culture of the Bacillus sp. VCHB-10 strain and the subsequent recovery of the bacterial aggregates obtained were carried out in the same manner as in Example 4.

The biomass stabilization process with polyethyleneimine and glutaraldehyde at 1% was executed in duplicate as described in Example 4, except that the solution of glutaraldehyde was incubated for 4 different lengths of time: 15, 30, 60 and 120 minutes.

The stabilized bacterial aggregates were used to carry out a process of biosorption of metals. For this, each fraction of stabilized biomass was submitted to the biosorption process according to the process described in Example 1. Subsequently, the total concentration presented in the aliquots of biosorption and desorption were measured in a Hanna Instruments® photometer, Series C99&C200.

Figure 9:
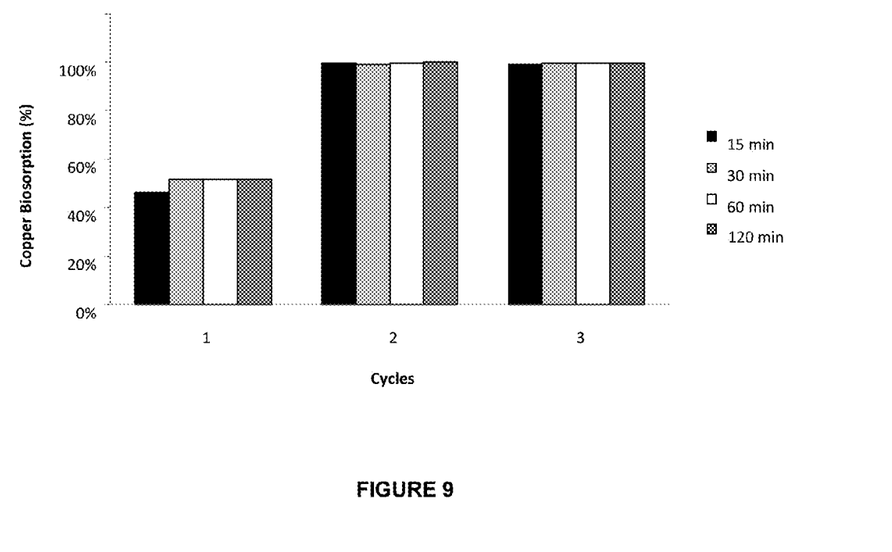
FIG. 9 shows the percentage of copper captured by the biomass stabilized and incubated with glutaraldehyde 1% v/v for 15, 30, 60 and 120 minutes.
Figure 10:
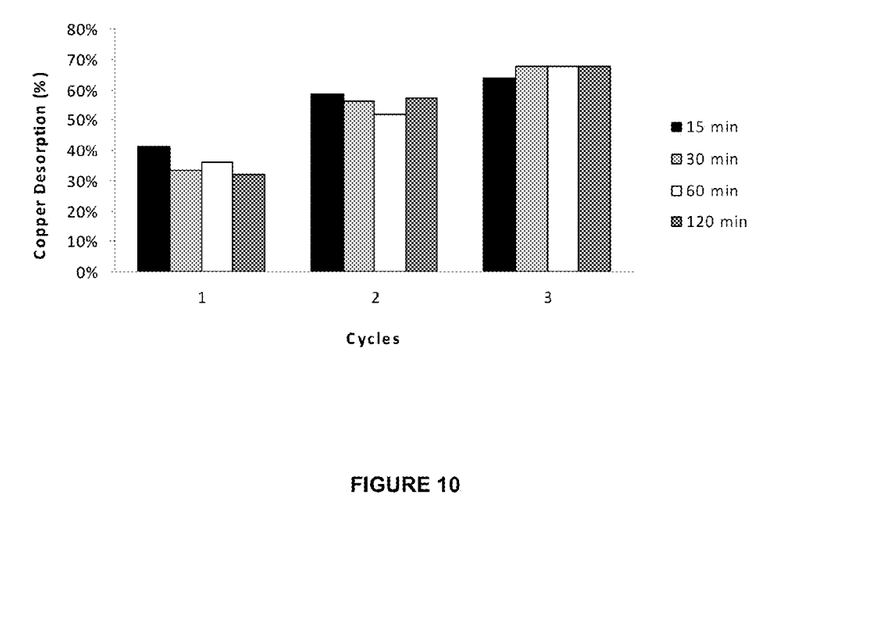
FIG. 10 shows the percentage of copper desorbed by the biomass stabilized and incubated with glutaraldehyde 1% v/v for 15, 30, 60 and 120 minutes.

The results obtained in this experiment show that the capacity of biosorption (FIG. 9) and of desorption (FIG. 10) was about the same for the different incubation times of incubation with the solution of glutaraldehyde in the three cycles analyzed.

Example 6

The culture of the Bacillus sp. VCHB-10 strain and the subsequent recovery of the bacterial aggregates obtained were carried out in the same manner as in Example 4.

The biomass recovered was separated into two experimental groups in duplicate, one corresponding to the control (without treatment) and the other corresponding to the treated biomass. For this last group, the stabilization process of the biomass with polyethyleneimine and glutaraldehyde at 1% was executed as described in Example 4. The resulting mixture was stirred gently and left to settle for 20 minutes, after which the bacterial aggregates were recovered in a separating funnel in the same manner as described previously.

The stabilized and non-stabilized bacterial aggregates were used to execute a metal biosorption process. For this, two 500 mL Erlenmeyer flasks were prepared in duplicate with 8 mL of stabilized and non-stabilized biomass, which were submitted to the biosorption process according to what is described in Example 1.

The stabilized and the non-stabilized biomass present in each cycle were estimated by means of the dry weight method. Finally, the dry weight was measured using an analytical balance. For this, an aliquot of 10 mL was taken from the mixture of biomass and copper solution prior to each decantation after the biosorption process. This biomass suspension was centrifuged at 8,000 rpm, the supernatant was eliminated and the pellet was left to dry at 105° C. for 24 hours. Because this aliquot of copper solution was taken, the volume used in each following cycle was reduced by 10 mL, in order to keep the biomass/solution ratio constant. This was also done proportionally with the volume of the solutions of sulfuric acid and of NaOH.

Figure 11:
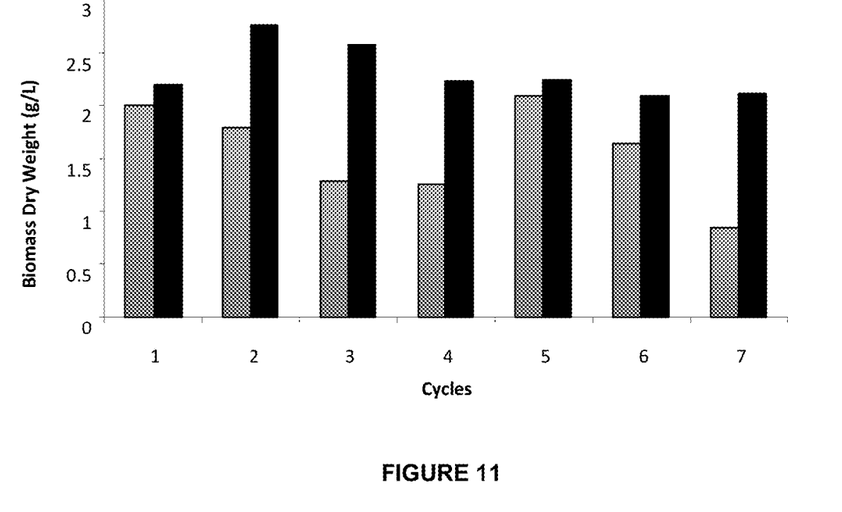
FIG. 11 shows the biomass dry weight, stabilized and not stabilized, in each cycle carried out.

FIG. 11 shows the estimated dry weight of the biomass, stabilized (black bars) and not stabilized (grey bars), in each cycle carried out. The bars in black correspond to the dry weight of the biomass including bacteria of *Bacillus* sp. (VCHB-10) treated with polyethyleneimine and glutaraldehyde, and the bars in grey correspond to the dry weight of biomass including bacteria of *Bacillus* sp. (VCHB-10) without treatment. During the entire course of the experiment, the dry weight of the stabilized (modified) biomass is greater than that of the non-stabilized (unmodified). The latter suffers a continuous loss of biomass from the second biosorption-desorption cycle to the fourth biosorption-desorption cycle and from the fifth biosorption-desorption cycle to the seventh biosorption-desorption cycle. On the other hand, the stabilized biomass shows a greater permanency during the 7 cycles studied.

Example 7

The culture of the *Bacillus* sp. VCHB-10 strain and the subsequent recovery of the bacterial aggregates obtained were carried out as described in Example 4.

The process of immobilization with a solution at 1% w/v of polyethyleneimine was carried out in 500 mL Erlenmeyer flasks by mixing 8 mL of flocculated biomass, 31.2 mL of methanol p.a. (Merck®) and 0.8 mL of a solution of polyethyleneimine 50% w/v (Sigma®) in duplicate for each one of the 5 different volumes of copper solution tested (300 mL, 450 mL, 600 mL, 750 mL, and 1000 mL). This mixture was gently shaken at room temperature for 24 hours and later combined with a solution made up of 8 mL of glutaraldehyde 25% w/v and 154 mL of distilled water, so that the latter finally remained at 1% v/v. After incubating this mixture for 20 minutes at room temperature, the bacterial aggregates were recovered in a separating funnel in the same manner as described in Example 1.

The stabilized bacterial aggregates were used to carry out a metal biosorption process. For this, prior to starting the biosorption process, each fraction of stabilized biomass was incubated at 150 rpm of agitation with 50 mL of a solution of sulfuric acid (pH 1) at 28° C. for 30 minutes. The biosorbent was decanted and subsequently washed with 33.3 mL of a solution of NaOH (pH 11). Then the bacterial aggregates were recovered in a separating funnel in the same manner described in Example 4.

The stabilized biomass was separated in 5 groups of 8 mL in duplicate, to start the biosorption process with volumes of copper solution 20 mg/L in duplicate: 300, 450, 600, 750 and 1000 mL. The mixture of biomass and copper solution was shaken for 30 minutes at 150 rpm and 28° C. The desorption process was made with 50 mL of a solution of sulfuric acid (pH 1). Subsequently the stabilized biomass was washed with 33.3 mL of a solution of NaOH (pH 11) for the neutralization. The recovery of the bacterial aggregates between each cycle was executed in a separating funnel in the same manner described in Example 4.

Subsequently, the total copper concentration present in the aliquots of biosorption and desorption was measured in a Hanna Instruments® photometer Series C99&C200.

Figure 12:
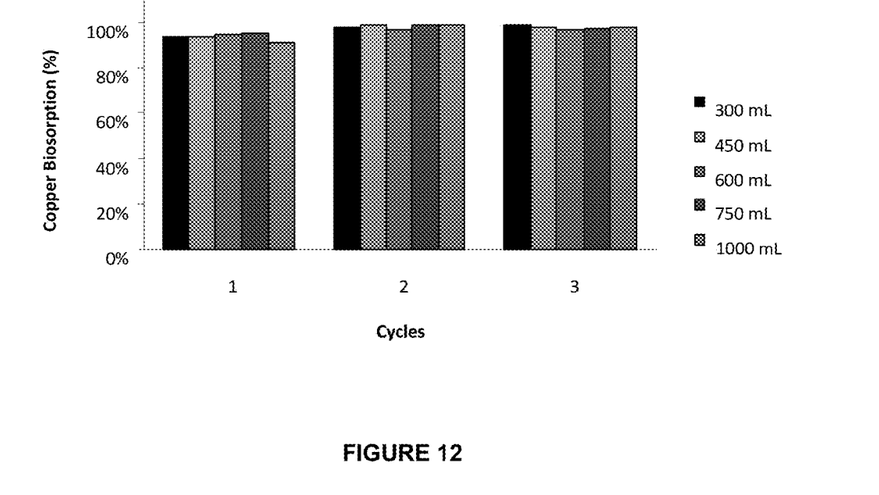
FIG. 12 shows the percentage of copper captured by the stabilized biomass incubated with 300, 450, 600, 750 and 1000 mL of copper solution.

FIG. 12 shows that the percentage of copper captured by the stabilized biomass in the first cycle is between 90% and 95%. This is nearly 30% higher than the total copper captured in the first cycle in the previous examples. This increase in the biosorption capacity may be due at least in part to the prior treatment of the biosorbent with the solution of sulfuric acid and NaOH, which may permit the activation of the sites of linkage to metals, an effect that in the previous examples is observed as of the second cycle. With regard to the other two cycles analyzed, the same figure shows that the biosorption reached is between 97% and 99%.

Figure 13:
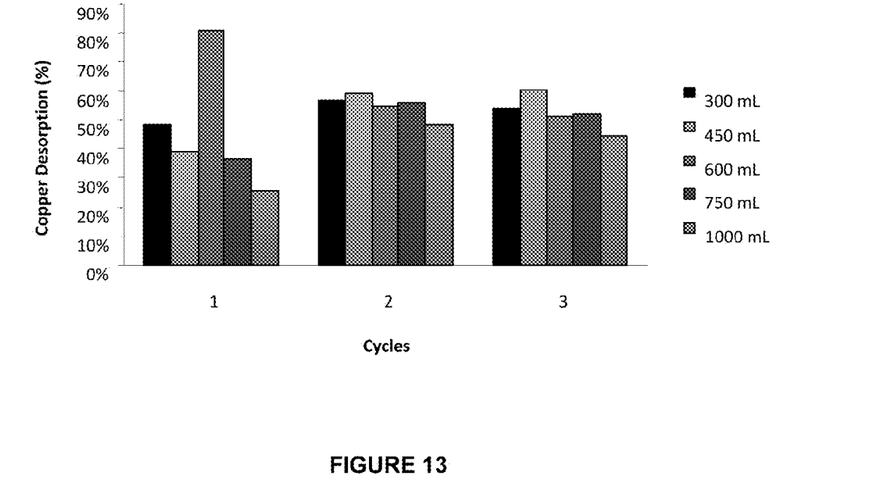
FIG. 13 shows the percentage of copper desorbed by the stabilized biomass incubated with 300, 450, 600, 750 and 1000 mL of copper solution.

FIG. 13 shows that although the volume of copper solution is increased, 50 mL of the sulfuric acid solution used is enough to recover, in all the cases, between 45% and 60% of the total copper.

Example 8

The cultivation of the *Bacillus* sp. VCHB-10 strain and the subsequent recovery of the bacterial aggregates obtained were executed as described in Example 4.

The biomass recovered was stabilized with polyethyleneimine and glutaraldehyde at 1% according to the description in Example 4. Then the bacterial aggregates were recovered in a separating funnel in the same manner as described in Example 4.

The stabilized bacterial aggregates were used to carry out a process of biosorption of zinc. For this, 10 mL of biomass recovered in duplicate was taken to then execute the biosorption process of the solution 20 mg/L of zinc in the form of heptahydrated zinc sulfate in a 500 mL Erlenmeyer flask.

Each fraction of stabilized biomass was submitted to the biosorption process according to the process described in Example 1. Subsequently, the total zinc concentration present in the aliquots of biosorption and desorption was measured in a Hanna Instruments® photometer Series C99&C200.

Figure 14:
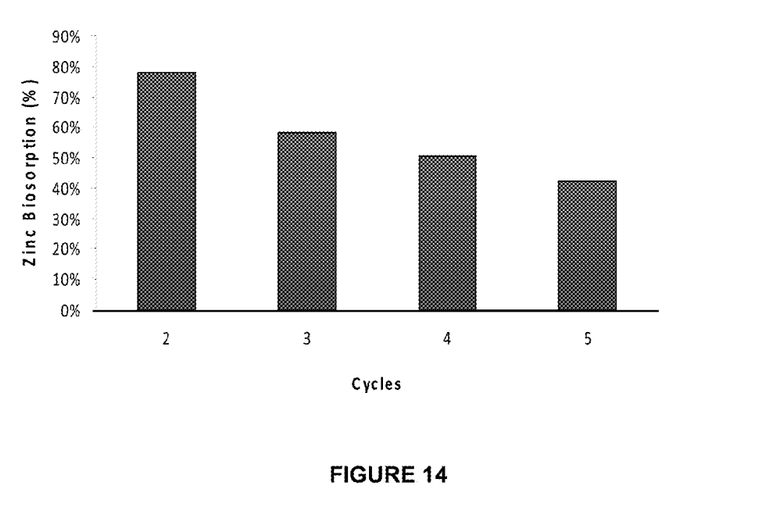
FIG. 14 shows the percentage of zinc captured by the stabilized biomass incubated with 120 mL of zinc solution.
Figure 15:
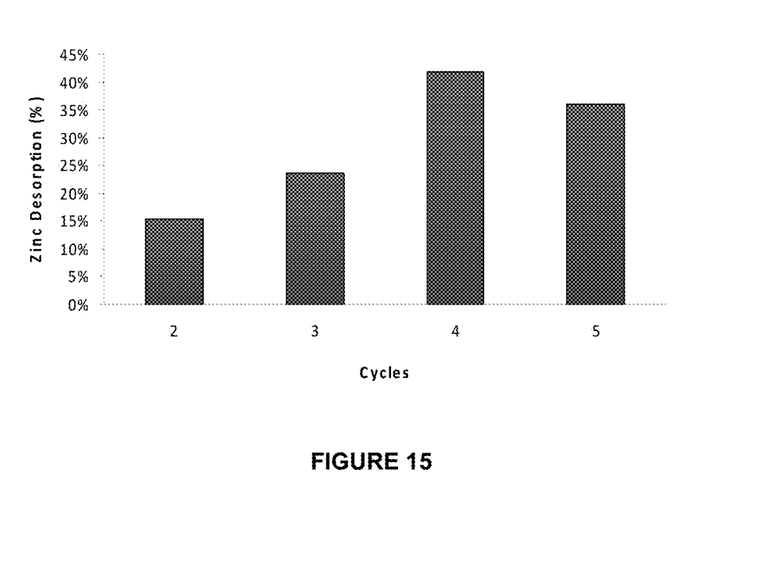
FIG. 15 shows the percentage of zinc desorbed by the stabilized biomass incubated with 120 mL of zinc solution.

FIG. 14 shows the percentage of zinc captured by the stabilized biomass incubated with 120 mL of zinc solution over four treatment cycles. FIG. 15 shows the percentage of zinc desorbed by the stabilized biomass incubated with 120 mL of zinc solution.

Example 9

The culture of the *Bacillus* sp. VCHB-10 strain and the subsequent recovery of the bacterial aggregates obtained were executed as described in Example 4.

80 mL of bacterial aggregates was recovered from the culture in the bioreactor and treated with a solution at 1% w/v of polyethyleneimine. This was executed in a 3 L Erlenmeyer flask, mixing the recovered aggregate biomass, 312 mL of methanol p.a. (Merck®) and 8 mL of a solution of polyethyleneimine 50% w/v (Sigme®). This mixture was gently agitated at room temperature for 24 hours to subsequently combined with a solution made up of 10 mL of glutaraldehyde 25% w/v and 1590 mL of distilled water, so that the latter finally remained at 1% v/v. The resulting mixture was incubated for 20 minutes to finally recover the bacterial aggregates by decantation.

Figure 16:
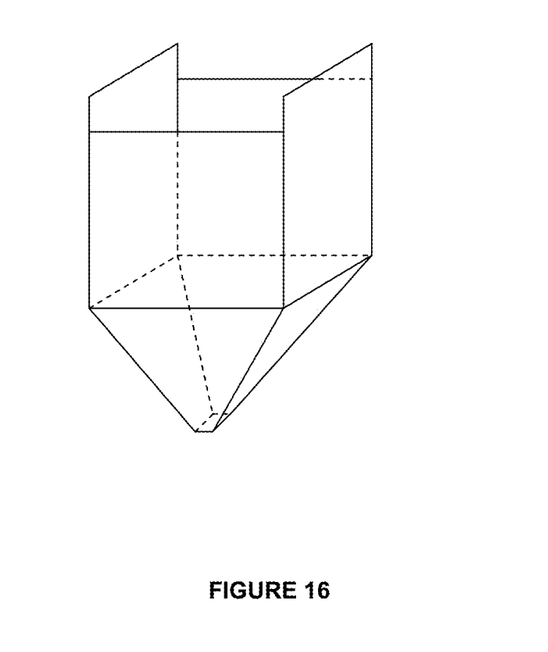
FIG. 16 shows a schematic representation of the Plexiglas® decanter having a capacity of 13 L, used for the biosorption-desorption experiments.

Finally, the stabilized biomass was transferred to a decanter vessel made of Plexiglas®, with a total capacity of 13 L, to carry out the biosorption-desorption experiments (FIG. 16).

The stabilized bacterial aggregates were used to carry out a process of metal biosorption. To do this, before starting the biosorption process, the stabilized biomass was treated at room temperature with 500 mL of a solution of sulfuric acid (pH 1.0) for 30 minutes. The agitation of the suspension was executed by means of aeration. For this, a tubing was installed in the lower part of the decanter, which provided 3000 mL/min of aeration. The supernatant was removed using a Masterflex® peristaltic pump after 30 minutes of decantation of the biomass and subsequently it was washed with 333 mL of a solution of NaOH (pH 11).

The biosorption was carried out at room temperature by adding 10 L of the copper solution 20 mg/L to the decanter that contained the biomass and it was shaken for 30 minutes by means of aeration. At the end of the biosorption stage the stabilized biomass that contained copper was allowed to settle for 30 minutes. The supernatant solution was removed using a Masterflex® peristaltic pump. The desorption was carried out in the same manner, incubating the biomass for 30 minutes by aeration with 500 mL of a solution of sulfuric acid (pH 1). Subsequently, the neutralization of the stabilized biomass was carried out with 330 mL of a solution of NaOH (pH 11). In each case the supernatant was extracted in the same manner as described previously. The biosorption-desorption cycle was repeated ten times. Finally, the total concentration of copper present in the aliquots of biosorption and desorption was measured in a Hanna Instruments® photometer Series C99&C200.

Figure 17:
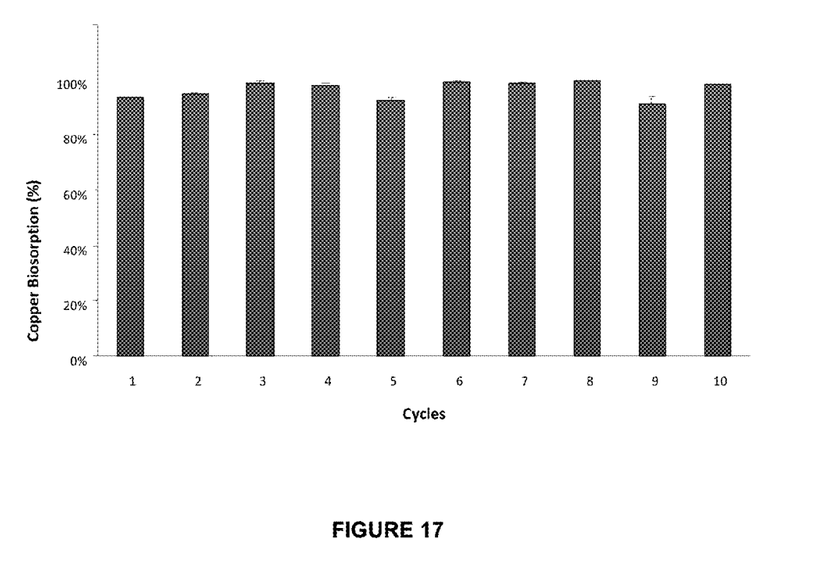
FIG. 17 shows the percentage of copper captured by the stabilized biomass incubated with 10 L of copper solution.
Figure 18:
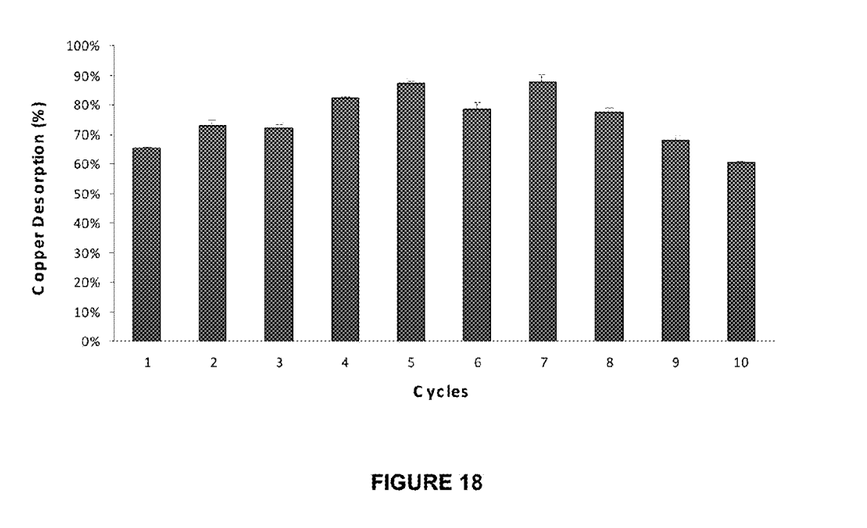
FIG. 18 shows the percentage of copper desorbed by the stabilized biomass incubated with 10 L of copper solution.

The results obtained in both the biosorption (FIG. 17) as well as the desorption (FIG. 18) where the biomass recovered nearly 100% of the copper, show that this new biosorbent is effective in the recovery of total copper from the 10 L with which the process was carried out. Thus, an even greater scaling may be possible.

What is claimed is:

1. A process for the production of a biosorbent for the removal of cationic or anionic metals from aqueous solution, the process comprising:
   a) growing the bacterial strain *Bacillus* sp. VCHB-10, deposited as NRRL-B-30881, under conditions sufficient to allow the bacterial strain to form aggregates of bacterial cells in a culture medium;
   b) allowing the aggregates of bacterial cells to sediment in order to concentrate the aggregates;
   c) recovering the concentrated aggregates;
   d) washing the concentrated aggregates with water;
   e) contacting the washed aggregates of concentrated bacterial cells with a solution of polyethyleneimine in methanol to form a reaction mixture, and allowing the mixture to undergo chemical modification;
   f) contacting the polyethyleneimine-treated aggregates with a solution of glutaraldehyde to initiate a crosslinking reaction;
   g) allowing the crosslinked aggregates to sediment; and
   h) washing the sedimented crosslinked aggregates with water to yield the biosorbent capable of adsorbing metal ions.

2. The process of claim 1, wherein the polyethyleneimine has a concentration in the reaction mixture between 0.5% and 10% w/v.

3. The process of claim 1, wherein the polyethylenemine has a concentration in the reaction mixture between 2% and 8% w/v.

4. The process of claim 1, wherein the polyethyleneimine has a concentration in the reaction mixture between 1% and 4% w/v.

5. The process of claim 1, wherein the solution of glutaraldehyde has a concentration between 0.1% and 2% v/v.

6. The process of claim 1, wherein the solution of glutaraldehyde has a concentration between 0.15% and 1.5% v/v.

7. The process of claim 1, wherein the solution of glutaraldehyde has a concentration between 0.2% and 0.5% v/v.

8. The process of claim 1, further comprising washing the biosorbent with an acid to form an acidic biomass.

9. The process of claim 8, wherein the acid is selected from the group consisting of sulfuric acid, hydrochloric acid and phosphoric acid.

10. The process of claim 8, further comprising neutralizing the acidic biomass with a base.

11. The process of claim 10, wherein the base is selected from the group consisting of sodium hydroxide (caustic soda) and potassium hydroxide (potash).

12. A biosorbent comprising bacterial aggregates of the bacterial strain *Bacillus* sp. -10, deposited as NRRL-B-30881, produced by the process of claim 1.

13. A biosorbent comprising bacterial aggregates of the bacterial strain *Bacillus* sp. VCHB-10, deposited as NRRL-B-30881, and modified with polyethyleneimine and glutaraldehyde.

14. The biosorbent of claim 13, wherein the biosorbent is capable of adsorbing metal ions from solution.

15. The biosorbent of claim 14, wherein the metal ions comprise metal cations selected from the group consisting of cations of Ag, Al, Au, Co, Cd, Cu, Cr, Fe, Hg, Mn, Ni, Pb, Pd, Pt, U, Th and Zn.

16. The biosorbent of claim 14, wherein the metal ions comprise metal anions selected from the group consisting of anions of As, Cr and Mo.

17. A process for the removal or recovery of metal ions from wastewater, the process comprising:
   a) contacting wastewater comprising metal ions with the biosorbent of claim 14 to adsorb the metal ions to the biosorbent by biosorption; and
   b) separating the biosorbent with adsorbed metal ions from the wastewater.

18. The process of claim 17, further comprising:
   c) contacting the biosorbent with adsorbed metal ions with an acid to elute the metal ions from the biosorbent.

19. The process of claim 18, further comprising repeating steps a, b, and c.

* * * * *

UNITED STATES PATENT AND TRADEMARK OFFICE
CERTIFICATE OF CORRECTION

PATENT NO. : 8,748,153 B2  
APPLICATION NO. : 13/105506  
DATED : June 10, 2014  
INVENTOR(S) : Davor Cotoras Tadic, Pabla Viedma and Juan Manuel Gajardo Sandoval Page 1 of 1

It is certified that error appears in the above-identified patent and that said Letters Patent is hereby corrected as shown below:

On the Title page, column 1 Item (56) (Other Publications), entry 10, line 28, delete "byPseudomonas" and insert -- by Pseudomonas --, therefore.

In the Claims

Claim 3, column 14, line 11, delete "polyethylenemine" and insert -- polyethyleneimine --, therefore.

Claim 12, column 14, line 33, delete "sp." and insert -- sp. VCHB --, therefore.

Signed and Sealed this  
Thirtieth Day of December, 2014

Michelle K. Lee  
*Deputy Director of the United States Patent and Trademark Office*